United States Patent
Baron

(10) Patent No.: US 10,076,484 B1
(45) Date of Patent: Sep. 18, 2018

(54) FORMULATION AND METHOD OF CONDITIONING SKIN AND PRESERVING COSMETICS APPLIED THERETO

(71) Applicant: Robert Baron, Millville, NJ (US)

(72) Inventor: Robert Baron, Millville, NJ (US)

( * ) Notice: Subject to any disclaimer, the term of this patent is extended or adjusted under 35 U.S.C. 154(b) by 0 days.

(21) Appl. No.: 15/583,259

(22) Filed: May 1, 2017

(51) Int. Cl.
| *A61K 8/34* | (2006.01) |
| *A61K 8/64* | (2006.01) |
| *A61K 8/73* | (2006.01) |
| *A61K 8/67* | (2006.01) |
| *A61K 8/31* | (2006.01) |
| *A61Q 1/00* | (2006.01) |
| *A61Q 1/02* | (2006.01) |

(52) U.S. Cl.
CPC .............. *A61K 8/735* (2013.01); *A61K 8/31* (2013.01); *A61K 8/34* (2013.01); *A61K 8/64* (2013.01); *A61K 8/676* (2013.01); *A61Q 1/00* (2013.01); *A61Q 1/02* (2013.01); *A61K 2800/43* (2013.01)

(58) Field of Classification Search
CPC ...... A61K 8/0204; A61K 8/046; A61K 8/735; A61K 8/64; A61K 8/34; A61K 8/31; A61Q 17/00; A61Q 17/04; A61Q 19/005; A61Q 19/08
See application file for complete search history.

(56) References Cited

U.S. PATENT DOCUMENTS

| 3,421,918 A | * | 1/1969 | Salzberg | A61K 8/64 |
| | | | | 106/146.4 |
| 5,002,076 A | * | 3/1991 | Altobelli | A61K 8/26 |
| | | | | 132/202 |
| 5,918,771 A | | 7/1999 | Van Der Heijden | |
| 6,451,286 B1 | | 9/2002 | Modi | |
| 6,503,479 B1 | | 1/2003 | LesAulnier et al. | |
| 2005/0136025 A1 | | 6/2005 | Pataut et al. | |
| 2007/0183994 A1 | * | 8/2007 | Kelly | A61K 8/06 |
| | | | | 424/59 |
| 2008/0311166 A1 | * | 12/2008 | Wimer | A61K 8/0208 |
| | | | | 424/402 |
| 2013/0251644 A1 | * | 9/2013 | Majhi | A61K 31/455 |
| | | | | 424/45 |
| 2014/0271518 A1 | | 9/2014 | Banowski et al. | |
| 2015/0073005 A1 | * | 3/2015 | Shimazaki | A61Q 7/00 |
| | | | | 514/275 |
| 2015/0166253 A1 | * | 6/2015 | Nomura | B65B 31/003 |
| | | | | 222/402.1 |

FOREIGN PATENT DOCUMENTS

| FR | 3006587 A1 | * | 12/2014 | ............ A61K 8/365 |
| JP | 2009292740 A | * | 12/2009 | |
| WO | WO 2003-041636 A2 | | 5/2003 | |
| WO | WO 2013-025916 A2 | | 2/2013 | |

OTHER PUBLICATIONS

HydraMist, Spray, Apr. 2017, 2 pages.
Matrixyl, The Dermatology Review, www.thedermreview.com/matrixyl/, 2017, accessed Feb. 28, 2017, 1 page.
Palmitoyl tetrapedide-7, The Dermatology Review www.thedermreview.com/palmitovl-tetrapeptide-7/, 2017, accessed Feb. 25, 2017, 3 pages.
The Latest Anti-Aging Crazes, New Beauty, newbeauty.com, Summer-Fall 2016, 1 page.

* cited by examiner

*Primary Examiner* — Jeffrey E Russel
(74) *Attorney, Agent, or Firm* — Baker & Hostetler LLP

(57) ABSTRACT

Disclosed are cosmetic spray and other formulations and methods for conditioning the skin and setting, preserving, or finishing cosmetics applied to the skin so as to immobilize cosmetics applied to the skin and to enhance the appearance of the cosmetics on the skin of the wearer.

17 Claims, No Drawings

FORMULATION AND METHOD OF CONDITIONING SKIN AND PRESERVING COSMETICS APPLIED THERETO

TECHNICAL FIELD

This invention relates to the use of a preservative or "finish" for cosmetic "make-up," and it particularly relates to a "finish" of this type which enhances the appearance of the "make-up" on the skin of the wearer and retains the "make-up" in place and in appearance for an extended period of time.

BACKGROUND

Many women throughout the world today use cosmetics, particularly on their faces. One of the problems, however, in the use of such cosmetics is that even though much time may be spent in the application thereof in order to obtain the most desirable appearance, the cosmetics, such as face powder, rouge or the like, may wear or "run" off because of the action of perspiration, rain, wind, abrasive dust, heat, humidity, activity, and other factors. Accordingly, there is a long-felt need in the art for compositions and related methods for fixing cosmetics in place.

SUMMARY OF THE INVENTION

It is one of the objects of the present invention to overcome the above and other problems inherent in the use of cosmetics by providing a cosmetic formulation and a method of application thereof which preserves the make-up, once it is applied to the skin, against rapid wear or deterioration despite the deleterious actions of moisture, wind, abrasive dust, and the like.

Another object of the present invention is to provide a cosmetic formulation and a method of application thereof which removes the undesirable "shine" from the "make-up" and provides a matte-like finish thereto.

Another object of the present invention is to provide a cosmetic formulation and a method of application thereof which, in addition to preserving the "make-up" on the skin, also acts to refresh the skin and to prevent the accumulation of dirt and dust thereon.

Another object of the present invention is to provide a cosmetic formulation and a method of application thereof which, in addition to the other functions noted above, serves to retain the pores of the skin in a relatively closed or diminished size, and thereby helps to prevent the clogging of the skin and the formation of blemishes and blackheads.

Another object of the present invention is to provide a cosmetic formulation that, while hydrating the skin, avoids the problems of excess moisture, dripping, or smearing, and feels "sensibly" dry to the touch within a few seconds of applying the cosmetic formulation. The formulations may also improve skin health and reduce the appearance of wrinkles, fine lines, and other imperfections.

In one aspect, the present disclosure provides cosmetic spray formulations, comprising: a denatured alcohol; at least one peptide; hyaluronic acid or a salt thereof and a cosmetically-acceptable propellant. The cosmetic spray formulation may additionally comprise assorted vitamins.

In another aspect, the present disclosure provides spray dispenser, the spray dispenser having disposed within an amount of a spray formulation according to the present disclosure, and being configured to spray the amount of the spray formulation.

In a further aspect, the present disclosure provides methods, the methods comprising spraying the skin with a formulation according to the present disclosure, conditioning the skin, and/or setting cosmetics applied to the skin, thereby retaining the cosmetics in place on the skin for an extended period of time.

Other objects of the present invention will become apparent from the following detailed description and claims.

DETAILED DESCRIPTION OF THE INVENTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms "a," "an," and "the" include plural referents unless the context clearly dictates otherwise. As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps. It is to be understood that the terminology used herein is for the purpose of describing particular aspects only and is not intended to be limiting. As used in the specification and in the claims, the term "comprising" can include the embodiments "consisting of" and "consisting essentially of." Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

Numerical values in the specification and claims of this application, particularly as they relate to polymers or polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams (g) to 10 grams" is inclusive of the endpoints, 2 grams and 10 grams, and all the intermediate values). The endpoints of the ranges and any values disclosed herein are not limited to the precise range or value;

they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

Weight percentages should be understood as not exceeding a combined weight percent value of 100 wt. %. Where a standard is mentioned and no date is associated with that standard, it should be understood that the standard is the most recent standard in effect on the date of the present filing.

In accordance with the present invention, during, or after applying cosmetics to the skin, but preferably after applying cosmetics to the skin, the cosmetics may be fixed or preserved in the desired form for an extended period of time, for example at least 2 to 4 times longer than the applied cosmetics and the intended appearance thereof would be retained without the cosmetic spray formulation of the present invention, by applying thereto a spray of a cosmetic formulation according to the presently described invention.

In one particular embodiment, the cosmetic formulation of the present invention comprises a denatured alcohol, e.g., an anhydrous denatured alcohol or even a specially denatured alcohol, such as, e.g., SDA 40B. Without being bound to any particular theory, the alcohol not only serves to cool the skin, but its coolness acts to diminish the size of the pores and to close them around the particles of cosmetics, whereby these particles become more closely held by the pores and are prevented from quickly falling or running off.

The application of the alcohol may be as a fine mist, such as is provided by a spray, because, following spraying of the cosmetic formulation of the present invention to the skin, the skin is "sensibly" dry to the touch within a short time after spraying the cosmetic formulation. As used herein, "sensibly" dry means dry to the touch within about 10 or fewer seconds, preferably 5 or fewer seconds, most preferably about 3 or fewer seconds from the time of spraying. In addition, spraying the cosmetic formulation according to the present invention may form a "breathing" or porous type of coating because of the close spacing of the fine particles of the sprayed mist.

In accordance with the present invention, the cosmetic formulation comprises at least one peptide. The peptide may be one or more oligopeptides. Suitable peptides include, e.g., a palmitoyl oligopeptide, including, for example, a palmitoyl dipeptide, a palmitoyl tripeptide, a copper tripeptide, a palmitoyl tetrapeptide, a palmitoyl pentapeptide, a palmitoyl hexapeptide, or a palmitoyl heptapeptide, or a combination thereof. Palmitoyl tetrapeptide-7 is considered especially suitable.

Again without being bound to any particular theory, inclusion of the peptide in the cosmetic formulation enhances skin health, hydration, and/or appearance. In some embodiments, the peptide is a collagen-active peptide, e.g., a peptide that encourages collagen activity in the skin to which the peptide is applied. Preferably, the at least one peptide of the presently disclosed formulation encourages collagen formation; reduces the appearance of fine lines or wrinkles; reduces the appearance of blemishes or discoloration, including rosacea; increases the presence of hyaluronic acid in the derma; hydrates the derma; or otherwise acts to improve the appearance or health of the skin. Without being bound to any particular theory, the presence of hyaluronic acid may increase the level (or appearance) of moisture in the treated skin.

The cosmetic formulation of the present invention may further comprise hyaluronic acid, or a cosmetically acceptable form or salt thereof. In addition, the cosmetic formulation may further comprise one or more vitamins, including, for example, Vitamin C, Vitamin K, Vitamin E, or Vitamin B5, or a combination thereof.

The cosmetic formulation of the present invention further comprises one or more cosmetically-acceptable propellants, e.g., propellant A31 or 152A or others. The formulation may comprise a combination of two or more propellants.

The cosmetic formulation of the present invention may further comprise fruit extracts, olive extracts, almond oil, aloe vera, lanolin, shea butter, or any other cosmetically-acceptable lipid, hydrocarbon, emollient, or any combination thereof.

In some embodiments, the cosmetic formulation of the present invention may be a cream, paste, or balm. As described herein, spray formulations are considered especially suitable.

For longer staying power it is often desirable, especially under hot lights, humid weather, or the like, to apply this spray after the "make-up" is applied; however, it will often be sufficient to apply this spray only after the "make-up" is applied.

It is important that the cosmetic formulation provide a "dry" sensation when applied. When the cosmetic formulation is applied in a fine spray, it provides a "dry" sensation when it touches the skin.

DETAILED DESCRIPTION OF ILLUSTRATIVE EMBODIMENTS

The following are exemplary embodiments of the presently disclosed invention. The exemplary embodiments are illustrative only and do not limit the scope of the present disclosure or the claims appended hereto.

Embodiment 1

A cosmetic spray formulation, comprising:
a denatured alcohol;
at least one peptide;
hyaluronic acid or a salt thereof; and
one or more cosmetically-acceptable propellants.

Embodiment 2

The cosmetic spray formulation of embodiment 1, wherein the at least one peptide is an oligopeptide, such as a palmitoyl dipeptide, a palmitoyl tripeptide, a copper tripeptide, a palmitoyl tetrapeptide, a palmitoyl pentapeptide, a palmitoyl hexapeptide, or a palmitoyl heptapeptide, or a combination thereof.

Embodiment 3

The cosmetic spray formulation of embodiment 2, wherein the at least one peptide is palmitoyl tetrapeptide-7.

Embodiment 4

The cosmetic spray formulation of embodiment 2, wherein the at least one peptide is palmitoyl pentapeptide-4.

Embodiment 5

The cosmetic spray formulation of any of embodiments 1-4, further comprising a vitamin.

Embodiment 6

The cosmetic spray formulation of embodiment 5, wherein the vitamin comprises Vitamin C, Vitamin K, Vitamin E, or Vitamin B5, or a combination thereof.

Embodiment 7

The cosmetic spray formulation of any of embodiments 1-6, wherein the propellant comprises a hydrocarbon, e.g., butane, isobutane, butane, isobutene, propane, isopentane, or any combination thereof; halogenated propellants are also considered suitable. A31 and 152A propellants are considered suitable, for example. Other cosmetically-acceptable propellants may be used, e.g., pressurized air, and the like.

Embodiment 8

The cosmetic spray formulation of any of embodiments 1-7, wherein the hyaluronic acid or salt thereof comprises sodium hyaluronate. The hyaluronic acid or salt thereof may have a molecular weight of less than about 500 kDa, in some embodiments. In other embodiments, the hyaluronic acid may comprise a polymer of hyaluronic acid that ranges in size from about 5,000 to about 20,000,000 Da.

Embodiment 9

The cosmetic spray formulation of embodiment 1, wherein:
the denatured alcohol is present at from about 1 to about 50 wt %, the peptide is present at from about 0.00001 to about 1 wt %, the hyaluronic acid is present at from about 0.00001 to about 1 wt %, the propellant is present at from about 50 to about 90 wt %, or any combination of (a), (b), (c), and (d).

The denatured alcohol may be present at from, e.g., about 1 to about 50 wt %, or from about 5 to about 45 wt %, or from about 10 to about 40 wt %, or from about 15 to about 35 wt %, or from about 20 to about 30 wt %, or even about 25 wt %. The peptide may be present at from, e.g., about 0.00001 to about 1 wt %, or from about 0.0001 to about 0.5 wt %, or from about 0.001 to about 0.3 wt %, or even from about 0.01 to about 0.1 wt %.

The hyaluronic acid may be present at from about 0.00001 to about 1 wt %, or from about 0.0001 to about 0.5 wt %, or from about 0.001 to about 0.3 wt %, or even from about 0.001 to about 0.1 wt %.

The propellant may be present at from about 50 to about 90 wt %, or from about 55 to about 85 wt %, or from about 60 to about 80 wt %, or from about 65 to about 75 wt %, or even at about 70 wt %.

Embodiment 10

The spray formulation of any of embodiments 1-9, wherein:
the denatured alcohol is SDA 40B, present at about 19.9997 wt %;
the peptide is palmitoyl tetrapeptide-7, present at about 0.0001 wt %;
the hyaluronic acid is sodium hyaluronate, present at about 0.0001 wt %;
the vitamin is Vitamin C, present at about 0.0001 wt %; and
the propellant is present at about 80 wt % and comprises A31 present at about 77 wt % and 152A present at about 3 wt % of the spray formulation.

Embodiment 11

The spray formulation of any of embodiments 1-10, further comprising a pigment. Suitable pigments include, e.g., mica, iron oxide, and other pigments.

Embodiment 12

The spray formulation of any of embodiments 1-11, further comprising a fragrance. Fragrances may comprise perfumes and the like; fresh-smelling fragrances (e.g., mint, citrus, botanical, and the like) may also be included.

Embodiment 13

The spray formulation of any of embodiments 1-12, further comprising a lipid, hydrocarbon, an emollient, or any combination thereof.

Embodiment 14

A spray dispenser, the spray dispenser having disposed within an amount of a spray formulation according to any of embodiments 1-13, and being configured to spray the amount of the spray formulation.

The dispenser may be a can, a bottle, a pump, and the like. The dispenser may be a one-use dispenser (which may be recycled), or a refillable dispenser. A dispenser may be configured to dispense one or more cosmetics and also dispense a formulation according to the present disclosure.

Embodiment 15

A method of conditioning the skin and setting cosmetics applied to the skin, thereby retaining the cosmetics in place on the skin, the method comprising spraying the skin with a formulation according to any of embodiments 1-13.

Embodiment 16

The method of embodiment 15, wherein the spraying follows application of cosmetics to the skin.

Embodiment 17

The method of embodiment 15, wherein the spraying is concurrent with application of cosmetics to the skin. This may be accomplished by, e.g., a dispenser that has dual nozzles, one for cosmetics and one for the disclosed composition. This may also be accomplished by a dispenser that has a single nozzle that dispenses both the cosmetic and the disclosed compositions simultaneously.

Embodiment 18

The method of any of embodiments 15-17, wherein the spraying effects hydrating the skin. Without being bound to any particular theory, the hydration may be accomplished by the hyaluronic acid, by the peptide, or by some other mechanism.

Embodiment 19

The method of any of embodiments 15-18, wherein, following spraying, the skin is sensibly dry to the touch within about 10, 5, or even fewer seconds from the time of spraying. It should be understood that a user may effect multiple applications of the presently disclosed formulations to their skin, e.g., before leaving for an event and during an event so as to "freshen up" their appearance.

Embodiment 20

A cosmetic formulation for setting or finishing cosmetics applied to the skin, the cosmetic formulation comprising:
optionally, a denatured alcohol;
at least one peptide; and
hyaluronic acid or a salt thereof.

The cosmetic formulation may be configured to be sensibly dry to the touch within about 5 or fewer seconds from the time of application.

Embodiment 21

The cosmetic formulation of embodiment 20, further comprising lanolin, shea butter, glycerin, sesame oil, menthol, glucose, an ultraviolet protectant, or any combination thereof.

The cosmetic formulation may be a gel, tincture, lotion, cream, or wash, or the like. The cosmetic formulation may be useful, for example, as a sun screen, an after-shave, a pre-shave lotion, or the like. The cosmetic formulation may be in an aerosol spray.

Without being bound to any particular theory, the disclosed compositions have the unexpected effect of inducing moisturizing of the skin without, in some embodiments, delivering excess moisture to the skin, which excess moisture may cause previously-applied cosmetic to run or drip. In this way, the disclosed compositions enable a user to induce moisture or "plumping" within the skin without also introducing unwanted excess moisture at the skin's surface.

The formulations may be composed in a variety of ways. In some embodiments, the formulations are configured such that the alcohol evaporates nearly immediately. In other embodiments, the formulations are configured such that the alcohol persists for a time, so as to lengthen the cooling sensation of the formulation. A formulation may include two or more ingredients of different volatilities so as to modulate the duration of the cooling sensation of the formulation, as well as the ability of the formulation to close the user's pores.

The present formulations may be present in a variety of forms. In a first form, the formulation may be a makeup finishing aerosol spray with wrinkle and fine line reduction benefits for the face and neck area. In another form, the formulation may be a wrinkle and fine line reducer, in the form of a peptide-including cream base, which base may not include propellant. The formulation may be present as an after-shave moisturizer with wrinkle and fine line reducer in an aerosol spray. Formulations may also be present as an after-shave moisturizer with wrinkle and fine line reducers, the moisturizer containing a fragrance, e.g., grapefruit, lily of the valley, rosemary, peppermint, or other fragrance, in the form of an aerosol spray.

The formulations may also be formulated as a so-called pre-shave for use with electric razors, the pre-shave including a fine line and wrinkle reducer. The formulation may also be present as a makeup finishing spray that includes wrinkle and fine line reducers, as well as a sunscreen ingredient. The sunscreen may be present so as to give rise to a formulation that has a SPF value of 10, 15, or greater. It should be understood that the disclosed formulations may be adapted for use by male or female users.

What is claimed:

1. A cosmetic spray formulation, comprising:
   a denatured alcohol;
   at least one peptide, wherein the at least one peptide is a palmitoyl dipeptide, a palmitoyl tripeptide, a copper tripeptide, a palmitoyl tetrapeptide, a palmitoyl pentapeptide, a palmitoyl hexapeptide, or a palmitoyl heptapeptide, or a combination thereof;
   hyaluronic acid or a salt thereof and
   one or more cosmetically-acceptable propellants.

2. The cosmetic spray formulation of claim 1, wherein the at least one peptide is palmitoyl tetrapeptide-7.

3. The cosmetic spray formulation of claim 1, wherein the at least one peptide is palmitoyl pentapeptide-4.

4. The cosmetic spray formulation of claim 1, further comprising a vitamin.

5. The cosmetic spray formulation of claim 4, wherein the vitamin comprises Vitamin C, Vitamin K, Vitamin E, or Vitamin B5, or a combination thereof.

6. The cosmetic spray formulation of claim 1, wherein the propellant comprises a hydrocarbon.

7. The cosmetic spray formulation of claim 1, wherein the hyaluronic acid or salt thereof comprises sodium hyaluronate.

8. The cosmetic spray formulation of claim 1, wherein:
   (a) the denatured alcohol is present at from about 1 to about 50 wt %,
   (b) the peptide is present at from about 0.00001 to about 1 wt %,
   (c) the hyaluronic acid is present at from about 0.00001 to about 1 wt %,
   (d) the propellant is present at from about 50 to about 80 wt %,
   or any combination of (a), (b), (c), and (d).

9. The spray formulation of claim 4, wherein:
   (a) the denatured alcohol is SDA 40B, present at about 19.9997 wt %;
   (b) the peptide is palmitoyl tetrapeptide-7, present at about 0.0001 wt %;
   (c) the hyaluronic acid is sodium hyaluronate, present at about 0.0001 wt %;
   (d) the vitamin is Vitamin C, present at about 0.0001 wt %; and
   (e) the propellant is present at about 80 wt %.

10. The spray formulation of claim 1, further comprising a pigment.

11. The spray formulation of claim 1, further comprising a fragrance.

12. The spray formulation of claim 1, further comprising a lipid, hydrocarbon, an emollient, or any combination thereof.

13. A method of conditioning the skin and setting cosmetics applied to the skin, thereby retaining the cosmetics in place on the skin, the method comprising spraying the skin with a formulation comprising:
- a denatured alcohol;
- at least one peptide;
- hyaluronic acid or a salt thereof; and
- one or more cosmetically-acceptable propellants.

14. The method of claim 13, wherein the spraying follows application of cosmetics to the skin.

15. The method of claim 13, wherein the spraying is concurrent with application of cosmetics to the skin.

16. The method of claim 14, wherein the spraying effects hydrating the skin.

17. The method of claim 14, wherein, following spraying, the skin is sensibly dry to the touch within about 5 or fewer seconds from the time of spraying.

\* \* \* \* \*